US00PP31551P3

(12) United States Plant Patent
Arts

(10) Patent No.: US PP31,551 P3
(45) Date of Patent: Mar. 17, 2020

(54) RASPBERRY PLANT NAMED 'SARAFINA'

(50) Latin Name: *Rubus idaeus*
Varietal Denomination: Sarafina

(71) Applicant: Niels Arts, Aalsmeer (NL)

(72) Inventor: Niels Arts, Aalsmeer (NL)

(73) Assignee: Aubuy B.V., DeKwakel (NL)

( * ) Notice: Subject to any disclaimer, the term of this patent is extended or adjusted under 35 U.S.C. 154(b) by 0 days.

(21) Appl. No.: 15/732,920

(22) Filed: Jan. 13, 2018

(65) Prior Publication Data

US 2018/0220565 P1 Aug. 2, 2018

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
See application file for complete search history.

(56) References Cited

PUBLICATIONS

UPOV hit on raspberry plant named 'ABB 120', QZ PBR 20170244, filed Jan. 27, 2017.*

* cited by examiner

*Primary Examiner* — Anne Marie Grunberg
(74) *Attorney, Agent, or Firm* — C. A. Whealy

(57) ABSTRACT

A new and distinct cultivar of Raspberry plant named 'Sarafina', characterized by its upright and somewhat bushy plant habit; freely branching habit; high fruit production; fruits are produced on prior and current seasons' canes; large light red purple-colored conical fruits; pleasant and sweet fruit taste; and good fruit postharvest longevity.

2 Drawing Sheets

Botanical designation: *Rubus idaeus.*
Cultivar denomination: 'SARAFINA'.

BACKGROUND OF THE INVENTION

The present Invention relates to a new and distinct cultivar of Raspberry plant, botanically known as *Rubus idaeus* and hereinafter referred to by the name 'Sarafina'.

The new Raspberry plant is a product of a planned breeding program conducted by the Inventor in Rossum, Gelderland, The Netherlands. The objective of the breeding program was to develop new Raspberry plants with good fruit quality, productivity, uniformity and postproduction longevity.

The new Raspberry plant originated from a cross-pollination made by the Inventor of a proprietary selection of *Rubus idaeus* identified as code number 48, not patented, as the female, or seed, parent with *Rubus idaeus* 'Advaberimar', disclosed in U.S. Reissue Pat. No. 46,031 and U.S. Plant Pat. No. 23,916, not patented, as the male, or pollen, parent in 2011. The new Raspberry plant was discovered and selected by the Inventor as a single plant from within the progeny of the stated cross-pollination in a controlled environment in Rossum, Gelderland, The Netherlands in early September, 2012.

Asexual reproduction of the new Raspberry plant by root cuttings in a controlled environment at Rossum, Gelderland, The Netherlands since the spring of 2013 has shown that the unique features of this new Raspberry plant are stable and reproduced true to type in successive generations of asexual reproduction.

SUMMARY OF THE INVENTION

Plants of the new Raspberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sarafina'. These characteristics in combination distinguish 'Sarafina' as a new and distinct Raspberry plant:

1. Upright and somewhat bushy plant habit.
2. Freely branching habit.
3. High fruit production.
4. Fruits are produced on prior and current seasons' canes.
5. Large light red purple-colored conical fruits.
6. Pleasant and sweet fruit taste.
7. Good fruit postharvest longevity; fruits do not darken in color after harvesting.

Plants of the new Raspberry differ primarily from plants of the female parent selection in number of flowers and fruits produced as plants of the new Raspberry produce more flowers per spray and more fruits per plant of the female parent selection.

Plants of the new Raspberry differ primarily from plants of the male parent, 'Advaberimar', in fruit color as plants of the new Raspberry produce lighter-colored fruits than plants of 'Advaberimar' selection.

Plants of the new Raspberry can be compared to plants of *Rubus idaeus* 'Advabereen', disclosed in U.S. Reissue Pat. No. 46,041 and U.S. Plant Pat. No. 23,915. In side-by-side comparisons, plants of the new Raspberry differ from plants of 'Advabereen' in the following characteristics:

1. Plants of the new Raspberry are not as freely branching as plants of 'Advabereen'.

2. Fruits of plants of the new Raspberry are heavier in weight and firmer than fruits of plants of 'Advabereen'.

BRIEF DESCRIPTION OF THE PHOTOGRAPHS

The accompanying colored photographs illustrate the appearance of the new Raspberry plant showing the colors as true as it is reasonably possible to obtain in colored reproductions of this type. Colors in the photographs may differ slightly from the color values cited in the detailed botanical description which accurately describe the colors of the new Raspberry plant.

The photograph on the first sheet is a side perspective view of typical fruiting plants of 'Sarafina'.

The photograph on the second sheet is a close-up view of a typical fruit of 'Sarafina'.

DETAILED BOTANICAL DESCRIPTION

The aforementioned photograph, following observations and measurements describe plants grown during the spring, summer and autumn in 10-liter containers in a polyethylene-covered greenhouse in Rossum, The Netherlands and under typical cultural practices of Raspberry plant production. During the production of the plants, day temperatures averaged 17° C. and night temperatures averaged 11° C. Plants were one year old when the photograph and description were taken. In the following description, color references are made to The Royal Horticultural Society Colour Chart, 1995 Edition, except where general terms of ordinary dictionary significance are used.

Botanical classification: *Rubus idaeus* 'Sarafina'.

Parentage:

*Female, or seed, parent.*—Proprietary selection of *Rubus idaeus* identified as code number 48, not patented.

*Male, or pollen, parent.*—*Rubus idaeus* 'Advaberimar', disclosed in U.S. Reissue Pat. No. 46,031 and U.S. Plant Pat. No. 23,916.

Propagation:

*Type.*—By root cuttings.

*Time to initiate roots, summer.*—About 12 to 14 days at temperatures about 15° C. to 17° C.

*Time to produce a rooted young plant, summer.*—About six weeks at temperatures about 15° C. to 17° C.

*Root description.*—Medium to thin in thickness, fibrous, typically brownish white brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Upright and somewhat bushy plant habit; vigorous growth habit; rapid growth rate.

*Plant height.*—About 1.8 to 2.2 meters.

*Plant diameter.*—About 40 cm.

Cane description:

*Prior season's canes.*—Length: About 110 cm. Internode length: About 7 cm. Color: Close to 165B, no anthocyanin observed. Time of vegetative bud burst: Mid March in The Netherlands. Length of vegetative bud: About 6 mm. Time of cane emergence: Early April in The Netherlands.

*Current season's canes.*—Length: About 210 cm. Internode length: About 7 cm. Color: Close to 143D, no anthocyanin observed. Time of vegetative bud burst: Early March in The Netherlands. Length of vegetative bud: About 1 cm. Time of cane emergence: April in The Netherlands.

*Strength.*—Strong.

*Aspect.*—Mostly erect.

*Texture.*—Smooth, glabrous; thorny.

*Color, developing.*—Close to 145B.

*Color, dormant.*—Close to 174B.

*Thorns.*—Density: About four per linear cm. Length: About 2 mm. Width: About 3 mm. Shape: Roughly deltoid. Apex: Acuminate, downwardly sloping. Base: Truncate. Margin: Entire. Color, immature and mature: Close to 183A.

Leaf description:

*Arrangement.*—Alternate; compound with typically three leaflets.

*Length, leaf.*—About 28 cm to 40 cm.

*Width, leaf.*—About 24 cm to 32 cm.

*Length, terminal leaflet.*—About 16 cm to 20 cm.

*Width, terminal leaflet.*—About 10 cm to 15 cm.

*Length, lateral leaflets.*—About 14 cm.

*Width, lateral leaflets.*—About 10 cm to 12 cm.

*Leaflet shape.*—Ovate; not overlapping.

*Leaflet apex.*—Cuspidate.

*Leaflet base.*—Cordate.

*Leaflet margin.*—Double serrate.

*Leaflet profile.*—Straight to convex.

*Leaflet texture, upper and lower surfaces.*—Smooth, glabrous; rugose.

*Leaflet venation.*—Pinnate.

*Leaflet color.*—Developing leaflets, upper surface: Close to 144A. Developing leaflets, lower surface: Close to 147B. Fully expanded leaflets, upper surface: Close to 147A; venation, close to 147A. Fully expanded leaflets, lower surface: Close to 148B; venation, close to 148D.

*Petioles.*—Length, leaf: About 9 cm to 13 cm. Diameter, leaf: About 3 mm. Length, terminal leaflet: About 3 cm. Diameter, terminal leaflet: About 3 mm. Length, lateral leaflets: About 3 mm. Diameter, lateral leaflets: About 3 mm. Texture, upper and lower surfaces: Sparsely prickled. Color, upper and lower surfaces: Close to 145C.

Flower description:

*Flower form and flowering habit.*—Single star-shaped flowers arranged in axillary sprays; freely flowering with about three to six flowers per spray and about seven to eight sprays per lateral branch; flowers face mostly outwardly; flowers not persistent.

*Fragrance.*—None detected.

*Natural flowering season.*—In The Netherlands, plants flower in late April on prior season's canes and in July on current season's canes.

*Flower buds.*—Length: About 5 mm to 10 mm. Diameter: About 5 mm to 10 mm. Shape: Roughly deltoid with acuminate apex. Color: Close to 141D.

*Flower diameter.*—About 1.8 cm.

*Flower depth (height).*—About 5 mm.

*Petals.*—Arrangement: Single whorl of five petals. Length: About 9 mm to 10 mm. Width: About 4 mm to 5 mm. Shape: Lanceolate. Apex: Obtuse. Base: Attenuate. Margin: Entire. Texture, upper and lower surfaces: Smooth, glabrous. Color: When opening and fully opened, upper surface: Close to 155D. When opening and fully opened, lower surface: Close to 155D.

*Sepals*.—Arrangement: Single whorl of five sepals forming a star-shaped calyx. Calyx length: About 2 cm to 2.5 cm. Calyx width: About 2 cm to 2.5 cm. Length: About 2 cm. Width: Proximally, about 1 cm; distally, about 2 mm. Shape: Deltoid. Apex: Acuminate. Margin: Entire. Texture, upper and lower surfaces: Slightly pubescent. Color: When developing, upper and lower surfaces: Close to 145B. Fully opened, upper and lower surfaces: Close to 145B.

*Peduncles*.—Length: About 5 cm to 10 cm. Diameter: About 1.5 mm. Strength: Strong. Aspect: About 30° from vertical. Texture: Prickled. Color: Close to 145A; no anthocyanin observed.

*Pedicels* (*flowers and fruits*).—Length: About 3 cm to 5 cm. Diameter: About 1.5 mm. Strength: Strong. Aspect: About 30° from peduncle axis. Texture: Prickled. Color: Close to 145B; no anthocyanin observed.

*Reproductive organs*.—Stamens: Quantity per flower: About 50 or more. Filament color: Close to 155D. Anther length: About 1 mm. Anther color: Close to 164C and 156C. Pollen color: Close to 196C. Pistils: Quantity per flower: About 80 to 100. Pistil length: About 5 mm. Stigma shape: Rounded. Stigma color: Close to 155D. Style length: About 5 mm. Style color: Close to 155D. Receptacles: Height: About 1 cm. Diameter: About 1 cm. Shape: Conical. Color: Close to 155D. Fruits (aggregate of drupelets): Quantity: One per flower. Length of fruiting lateral: About 70 cm on prior and current seasons' canes. Fruiting lateral aspect: About 45° from vertical on prior and current seasons' canes. Number of drupelets per fruit: About 90 to 120. Time of fruit ripening: In The Netherlands, on prior season's canes, fruits ripen in late May, and on current season's canes, fruits ripen in September. Length of fruiting period: In The Netherlands, on prior season's canes, fruits are produced for about seven weeks, and on current season's canes, fruits are produced for about 56 to 70 days. Length: About 2 cm to 2.2 cm, fruits produced on prior season's canes are slightly larger than fruits produced on current season's canes. Diameter: About 1.8 cm to 2.2 cm. Shape: Broadly conical. Weight: About 6 to 7 grams. Firmness: Firm. Taste: Pleasant, sweet. Luster: Glossy. Adherence to plug: Moderately strong on both prior and current seasons' canes. Postharvest longevity: Good postharvest longevity, fruits last up to eleven days; fruits do not darken in color after harvest. Color: Close to 61B, 61C and 63A. Seeds: Quantity: One per drupelet. Length: About 2.5 mm. Diameter: About 1 mm. Texture: Smooth, glabrous. Color: Close to 20D.

Pathogen & pest resistance: Plants of the new Raspberry have been noted to be resistant to Yellow Rust (*Phragmidium rubi-idaei*), Downy Mildew (*Peronospora sparsa*) and Red Spider Mites (*Tetranychus urticae*).

Temperature tolerance: Plants of the new Raspberry have been observed to tolerate temperatures ranging from 4° C. to 35° C.

It is claimed:

1. A new and distinct Raspberry plant named 'Sarafina' as illustrated and described.

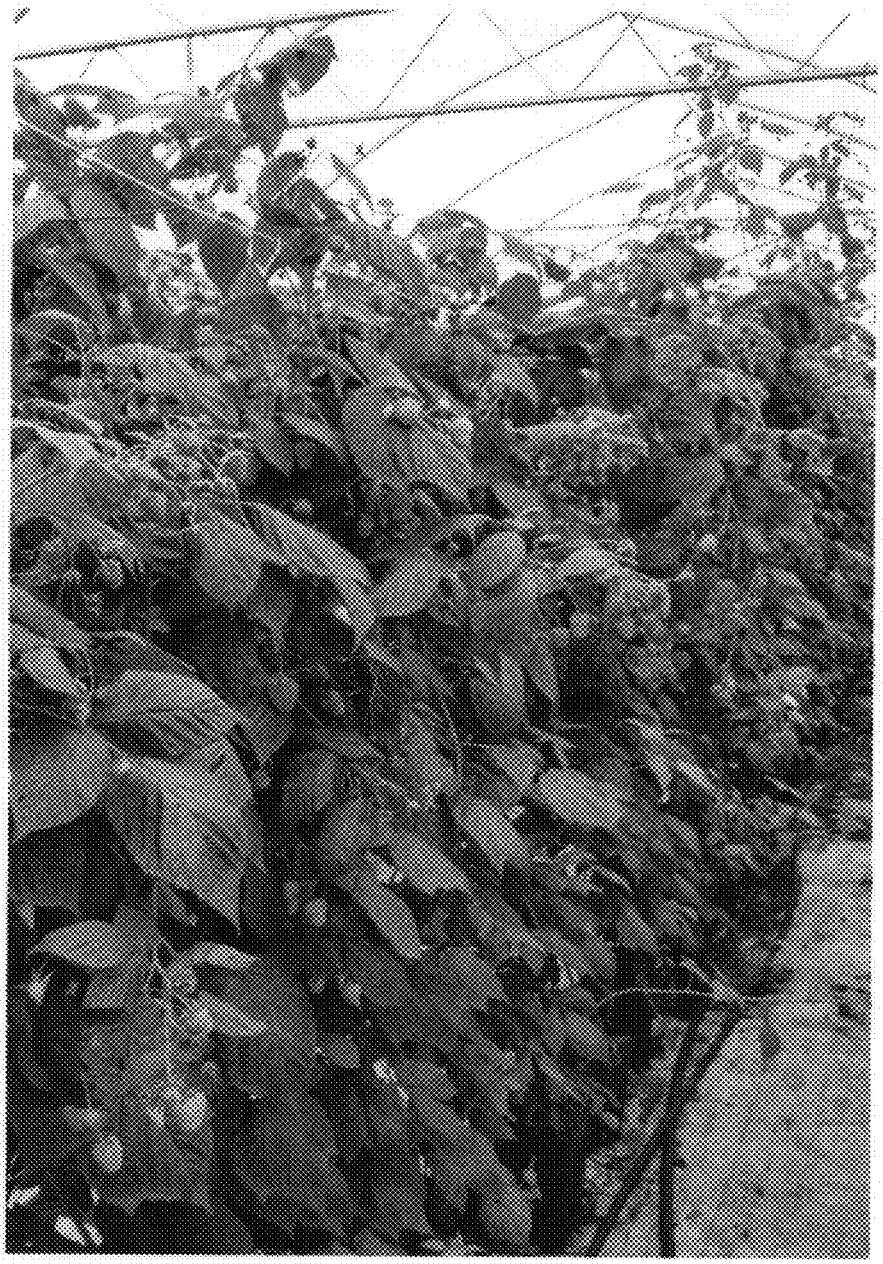

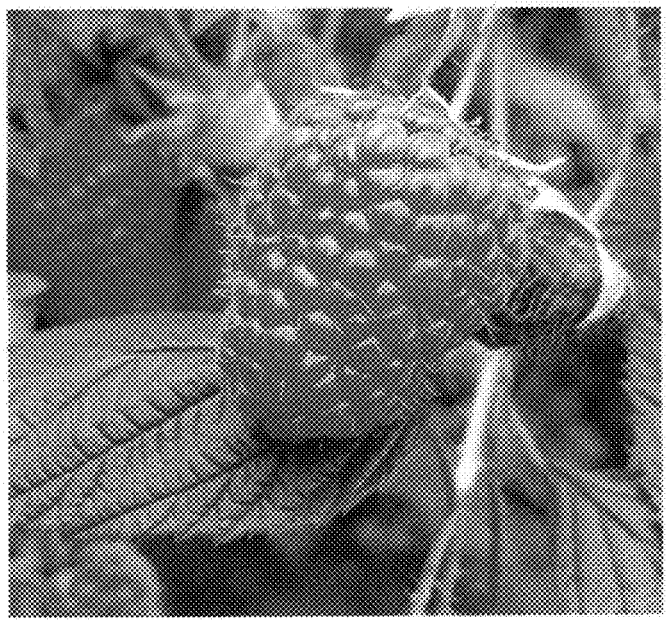

* * * * *